(12) United States Patent
Görne et al.

(10) Patent No.: US 9,173,974 B2
(45) Date of Patent: Nov. 3, 2015

(54) HYDROPHILIZING PLASMA COATING

(71) Applicant: BIOENERGY CAPITAL AG, Köln (DE)

(72) Inventors: Martin Görne, Hamburg (DE); Thomas Kordick, Goldbach (DE)

(73) Assignee: Bioenergy Capital AG, Cologne ( * ) Notice: Subject to any disclaimer, the term of this patent is extended or adjusted under 35 U.S.C. 154(b) by 0 days.

(21) Appl. No.: 14/351,504

(22) PCT Filed: Feb. 1, 2013

(86) PCT No.: PCT/EP2013/000329
§ 371 (c)(1),
(2) Date: Apr. 11, 2014

(87) PCT Pub. No.: WO2013/113518
PCT Pub. Date: Aug. 8, 2013

(65) Prior Publication Data
US 2014/0336758 A1    Nov. 13, 2014

(30) Foreign Application Priority Data
Feb. 1, 2012 (EP) .................... 12000648

(51) Int. Cl.
*B05D 1/00* (2006.01)
*G02C 7/04* (2006.01)
*A61F 2/16* (2006.01)
*A61L 27/34* (2006.01)
*B05D 3/14* (2006.01)
*B05D 5/04* (2006.01)
*B05D 3/04* (2006.01)
*B05D 7/00* (2006.01)

(52) U.S. Cl.
CPC .............. *A61L 27/34* (2013.01); *A61F 2/1613* (2013.01); *B05D 1/62* (2013.01); *B05D 3/144* (2013.01); *B05D 5/04* (2013.01); *G02C 7/049* (2013.01); *B05D 1/60* (2013.01); *B05D 3/0466* (2013.01); *B05D 7/54* (2013.01); *B05D 2201/00* (2013.01); *B05D 2502/00* (2013.01); *Y10T 428/264* (2015.01); *Y10T 428/31913* (2015.04)

(58) Field of Classification Search
CPC ......... A61F 2/1613; A61L 27/34; B05D 1/60; B05D 1/62; B05D 2201/00
See application file for complete search history.

(56) References Cited

U.S. PATENT DOCUMENTS 5,080,924 A * 1/1992 Kamel et al. ................. 427/2.24
6,005,160 A   12/1999 Hsiue et al.
(Continued)

FOREIGN PATENT DOCUMENTS

EP      0896035      2/1999
EP      0896035 A2 * 2/1999 ............... C09D 4/00
WO      99/57177     11/1999

OTHER PUBLICATIONS

International Search Report for International Patent Application PCT/EP2013/000329 mailed Mar. 18, 2013.

*Primary Examiner* — Dah-Wei D Yuan
*Assistant Examiner* — Kristen A Dagenais
(74) *Attorney, Agent, or Firm* — Morris & Kamlay LLP

(57) ABSTRACT

The invention relates to a method for hydrophilizing surfaces of polymer workpieces. The method has a step (a) of pretreating the workpiece surfaces in a high-frequency gas plasma which is produced on the basis of an inert gas in order to clean and activate the workpiece surfaces; a step (b) of precoating the pretreated workpiece surfaces with polyacrylic acid using a high-frequency gas plasma made of a gas mixture, said gas mixture being composed of an inert gas and a first gas made of biocompatible, polymerizable carboxy group-containing monomers; and a step (c) of subsequently coating the precoated workpiece surfaces using a second gas substantially containing acrylic acid monomers.

19 Claims, 3 Drawing Sheets

(56) References Cited

U.S. PATENT DOCUMENTS

Figure 1:
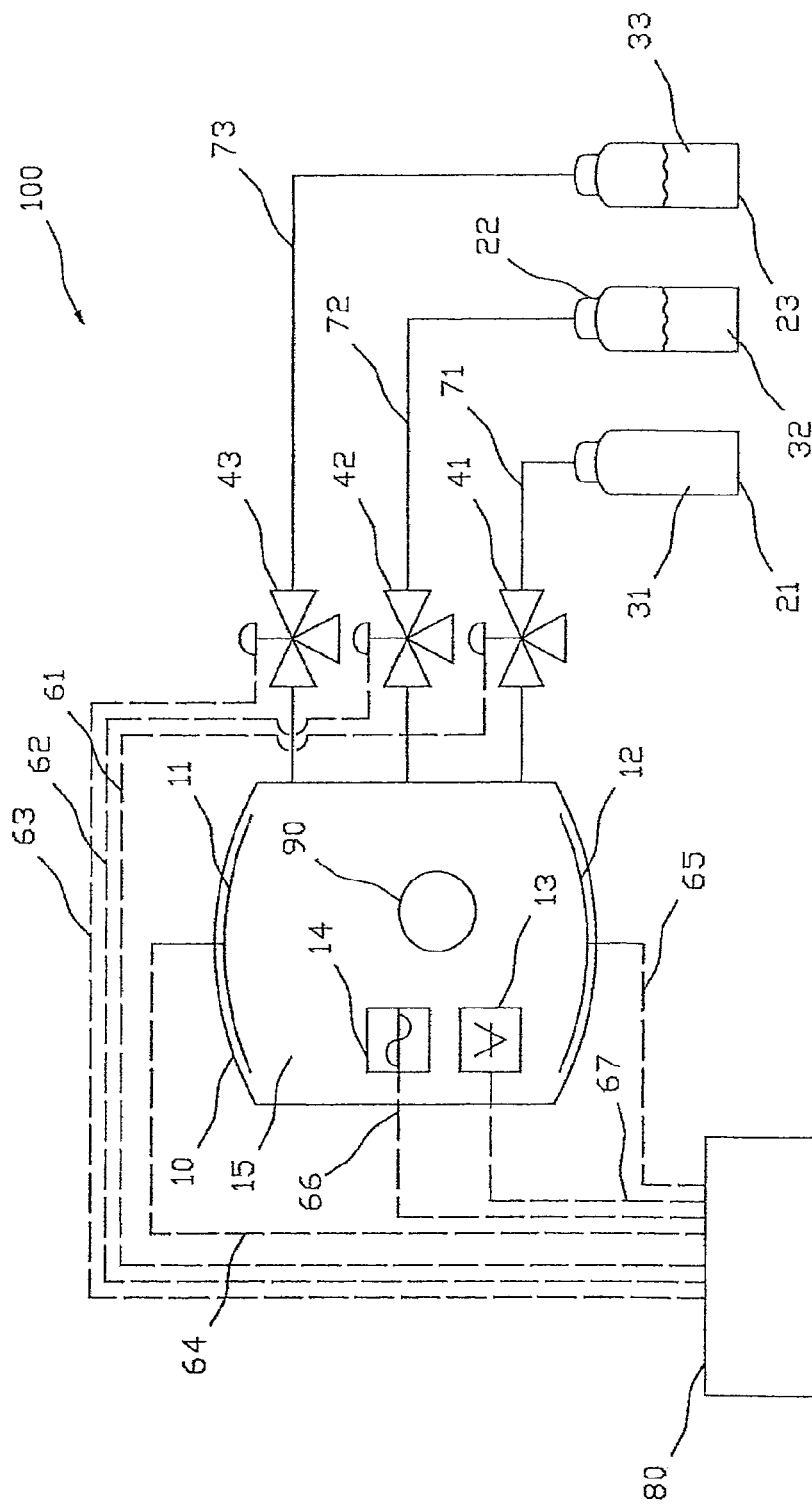

| | | |
|---|---|---|
| 6,610,350 B2 | 8/2003 | Suzuki et al. |
| 2008/0002146 A1* | 1/2008 | Stachowski et al. ...... 351/160 H |
| 2008/0208334 A1* | 8/2008 | Jinkerson et al. ............ 623/6.16 |
| 2008/0213460 A1* | 9/2008 | Benter et al. ................... 427/2.1 |
| 2009/0069790 A1* | 3/2009 | Yokley et al. ................. 604/523 |
| 2009/0305417 A1* | 12/2009 | Short et al. ..................... 435/402 |
| 2010/0035074 A1* | 2/2010 | Cohen et al. ................... 428/500 |
| 2010/0072642 A1* | 3/2010 | Broad et al. ................... 264/2.6 |

* cited by examiner

HYDROPHILIZING PLASMA COATING

The present invention relates to the surface treatment of workpieces on the basis of biomaterials and in particular relates to the permanent hydrophilizing of surfaces of such workpieces by means of plasma enhanced chemical vapour deposition (PECVD) and subsequent chemical vapour deposition (CVD).

There are high requirements to the biological compatibility of workpieces intended for temporary or permanent use in human or animal organs, such as e.g. contact lenses or implants, in order to avoid inflammatory processes. In order to accordingly ensure a high biocompatibility, the materials employed for manufacturing such workpieces have properties predestining them both for the respective use as also for the ensuing tissue contact.

The biological compliance of materials, also termed bio-compatibility, is determined to a large extent by their surface properties. For contact lenses, a hydrophilic surface is decisive for a good bio-compatibility. For implants in the context of Tissue Engineering (build-up of autologous tissue), a hydrophilic surface of polymeric scaffold substances improves their being colonized by tissue cells and, thereby, the therapeutic success. Also, in in vitro testing methods with vital cells, a hydrophilic surface of the polymeric substrate is advantageous for fixing the cells.

A biocompatible hydrophilizing of surfaces of polymeric bio-materials may be achieved by a modification of the polymeric surface by means of plasma oxidation, as described e.g. in the international application WO 99/57177. It turned out, however, that such hydrophilized surfaces are not sufficiently long-term stable.

A more permanent hydrophiliation of polymeric biomaterial surfaces is achieved by coating same with a hydrophilic biocompatible material. In order to manufacture hydrophilic surfaces on contact lenses made of polymethylmethacrylate (PMMA), in the patent document U.S. Pat. No. 5,080,924 e.g. a plasma deposition process for graft polymerising the surfaces with polyacrylic acid has been suggested. The graft polymerised PMMA-surfaces showed contact angles of water in the range of 35 to 50 degrees and are too large for a sufficient wetting of the material's surface. For further reducing the contact angle, the coating needs to be post-treated, e.g. by applying a further biocompatible material different from polyacrylic acid, which cross-links to the polyacrylic acid. Such a process involving coating plural layers requires a higher apparative effort and also results in longer coating times.

Starting out from what has been described above, it is therefore desirable to provide a less complex coating of polymeric biomaterials which enables a long-term stable surface hydrophilation with water contact angles of 15 degrees or less.

Such coating comprises a process for hydrophilizing surfaces of polymeric workpieces, wherein the process comprises a step (a) of cleaning and activating the work piece surfaces in the course of a pre-treatment with a high-frequency gas plasma formed on the basis of an inert gas, a step (b) of pre-coating the pre-treated workpiece surfaces with polyacrylic acid using a high-frequency gas plasma formed from a gas mixture, wherein the gas mixture is composed of an inert gas and a first gas formed of biocompatible, polymerizable carboxy group containing monomers, and a step (c) of follow-up-coating the pre-coated workpiece surfaces using a second gas substantially containing acrylic acid monomers.

The coating further comprises providing a polymeric workpiece with a hydrophilizing surface coating of polyacrylic acid, obtainable by a process comprising the steps specified above, wherein the contact angle of water on the workpiece surface coated with polyacrylic acid has a value in the range of 2 to less than 10 degrees.

The workpieces coated with the specified process have a long-term stable hydrophilic surface with excellent wettability, which in contact with body tissue results in a good bio compatibility, whereby irritations of the eye occur less frequently with accordingly coated contact lenses, and body cells more readily attach to accordingly coated scaffold substances for Tissue Engineering.

If not clearly intended differently from the context, the words "having", "comprising", "including", "encompassing", "with" and the like in the specification and the claims as well as their grammatical modifications are to be understood as comprising as opposed to exclusive or exhaustive meaning; i.e. in the sense of "including, but not limited to".

In preferred embodiments of the process, the biocompatible polymerizable monomers forming the first gas are selected from (meth)acrylic acid and (meth)acrylic acid anhydride, whereby in the high frequency plasma a large proportion of acrylic acid monomers is generated which attach to the workpiece surface activated in step (a) of the process forming covalent bonds.

In other preferred embodiments, the gas used in step (a) of the process for generating the high-frequency plasma contains the first gas in an amount corresponding to a partial pressure of less than one tenth of the partial pressure of the inert gas, so that an efficient cleaning and activating of the workpiece surfaces is ensured.

In order to achieve a stable attachment of the acrylic acid monomers to the workpiece surface, in preferred embodiments in step (b) a gas mixture is used in which the partial pressure of the first gas is at least one fourth of, and maximally twice the partial pressure of the inert gas.

With a view to obtaining a dense and stable poly(acrylic acid) coating, the partial pressure of the inert gas in the second gas used in step (c) is, in embodiments, less than one tenth of the partial pressure of the acrylic acid monomer-forming gas.

In embodiments, Argon is used as the inert gas.

For an efficient control of the pre-coating process, in embodiments the coating applied in step (b) is monitored by means of a layer thickness control device, and the process terminated upon reaching a layer thickness value selected from the range 50 to 400 Å.

In particularly preferred embodiments, in which contact angles in the range of 2 to less than 10 degrees are achieved, the pressure of the inert gas for the high-frequency plasma in step (a) is set to a value in the range 15 to 60 mTorr (ca. 2 to 8 Pa) and the pressure of the first gas for the high-frequency plasma in step (b) to a value in the range 30 to 90 mTorr (ca. 4 to 12 Pa).

For fixing the acrylic acid polymer coating on the workpiece surfaces, embodiments further include a step (cb), comprising throttling the inert gas supply and supplying a second gas immediately subsequent to step (b), wherein the pressure of the second gas in step (cb) is less than 0.3 mTorr (ca. 40 mPa).

In order to promote the attachment to, and cross-linking of acrylic acid monomers with the pre-coated workpiece surface, embodiments further comprise a step (bc), carried out immediately after step (b) or, if executed, step (cb), which further step comprises a switching-off of the high-frequency plasmas, an interrupting of the inert gas supply, and a supplying of the second gas, wherein the pressure of the second gas in step (c) is between 1.5 and 6 Torr (ca. 0.13 to 0.8 kPa).

In order to improve the bio-compatibility, embodiments comprise a step (d) subsequent to step (c) of removing water soluble components from the hydrophilizing layer by means of rinsing the coated workpiece in hydrophilic solvent, such as e.g. in isotonic saline solution or, depending on the intended application of the workpiece, in de-mineralized water.

In further preferred embodiments, the workpiece comprises, at least at its surface, a material which is formed mainly or substantially of a silicone, in particular poly(dimethylsiloxane), a silicone hydrogel, or a porous bioresorbable polymer such as PLA or PLGA. The thickness ranges of the workpieces in embodiments relating to the first case relevant for contact lenses are preferably between 50 and 300 µm, between 5 and 40 µm, or between 2 and 12 µm. The thickness of the coating in embodiments with porous PLA or PLGA is preferably between 5 and 40 nm.

In embodiments, the workpieces are silicone contact lenses. The hydrophilizing surface coating of these workpieces is comprised of a PAA-layer with an average thickness of 5 to 40 µm.

In other embodiments, the workpieces are a porous matrix of poly($\alpha$-hydroxycarboxylic acids). The hydrophilizing surface coating of these workpieces is comprised of a PAA-layer with an average thickness of 5 to 40 nm.

Figure 2:
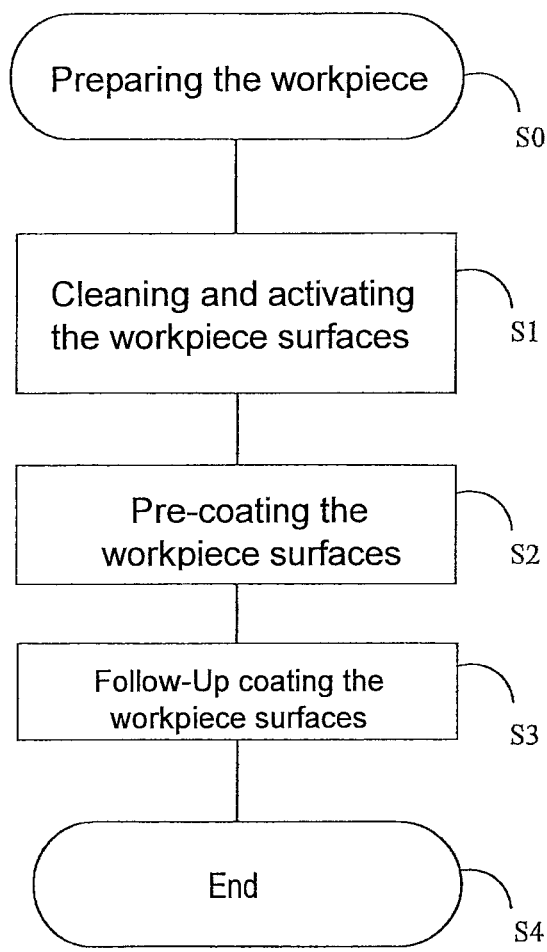
Figure 3:
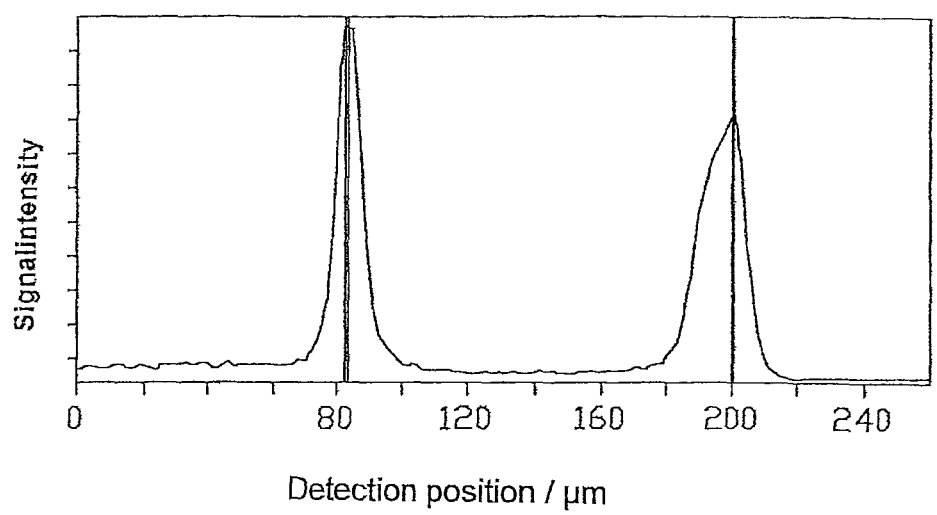

Further features of the invention are apparent from the following description of embodiments in conjunction with the claims and the drawings. The invention is not limited by the described embodiments, but determined by the scope of the appended claims. In particular, the individual features of embodiments according to the invention may be realized in a different number or combination than in the examples described below. In the following explanation of embodiments, reference is made to the appended drawings, which show:

FIG. 1 a schematic depiction for illustrating a system for biocompatibly coating of polymeric biomaterials;

FIG. 2 a flow diagram for illustrating the essential process steps for coating polymeric biomaterials with poly(acrylic acid); and FIG. 3 a fluorescence diagram for illustrating the layer thickness achievable with the process according to FIG. 2.

The scheme shown in FIG. 1 illustrates important components of an apparatus 100 for coating polymeric workpieces 90 with a material rendering their surfaces hydrophilic. The workpieces are preferably either contact lenses and in this case particularly those made of a silicone or a silicone hydrogel, or else a polymeric scaffold, preferably made of PLA (polylactide) or PLGA (polylactide-co-glycolide), suitable for Tissue Engineering.

The apparatus 100 comprises an evacuatable recipient 10 with a device for generating a high-frequency plasma in the interior 15 of the recipient 10. The device for generating a high-frequency plasma is symbolized in the scheme of FIG. 1 by means of two electrodes 11 and 12, but is not limited to the use of electrodes. It should be noted that in FIG. 1, for the sake of clarity and conciseness, only such components are depicted which are deemed to be required for understanding the invention. Such components as e.g. pumps for evacuating the recipient 10, which are required for operating the apparatus but are irrelevant for understanding the invention, are deemed present despite not being shown in the drawing. At least a vacuum or low pressure gauge 13 and a coating application measuring device 14, such as an oscillating quartz, are associated with the interior 15 of the recipient 10.

The coating apparatus 100 further includes an inert gas reservoir 21 and one or more coating material reservoirs 22 and 23. Each of the reservoirs or reservoir containers 21, 22 and 23, respectively, is connected by an associated one of ducts 71, 72 and 73 with the recipient 10 in such a manner that gaseous or vaporized substances kept in the reservoirs or reservoir containers can be guided into the interior 15 of the recipient 10. Control valves 41, 42 and 43 arranged in the ducts 71, 72 and 73 enable regulation of the flow of the respective gas or vapour into the recipient 10. In the embodiment shown, the control valves may alternatively be used for venting the reservoirs 21, 22 and 23. In other embodiments, separate valves and, if desired, separate ducts are employed for this purpose.

The apparatus 100 further includes a control 80, which is adapted for controlling or, if desired, regulating the coating processes e.g. by means of control leads 61, 62, 63, 64, 65 and signal leads 66 and 67. Depending on the requirements, the control can be adapted for a fully automatic or a semi-automatic coating control. It may be noted that, deviating from German use of the terms, in this text it is not discriminated between controlling and regulating. Instead, both terms are used synonymously, i.e. the term control may comprise returning a control quantity or its measured value, respectively, in the same manner as the term regulating may refer to a simple control chain. This also applies to grammatical variations of these terms. A regulating (partial) control of the apparatus 100 may be realized e.g. using the output signals from sensor devices associated with the interior 15. For example, the valves 41, 42 and 43 may be controlled, using the vacuum or low pressure gauge 13 in such a manner that in the interior 15 of the recipient 10 a predetermined constant gas or vapour pressure with likewise predetermined partial pressures is maintained. Furthermore, the control device 80 may be adapted to monitor the building-up of the coating by means of the coating thickness monitoring device 14 and to terminate same when a desired coating thickness is reached. In addition, the control 80 is typically arranged for controlling the high-frequency apparatus 11 and 12 in dependence of the process requirements.

The flow diagram 200 of FIG. 2 illustrates the important steps of a process for hydrophilizing workpiece surfaces by coating with poly(acrylic acid). Preferably, polymeric biomaterials are used for manufacturing the workpieces 90 or their surface regions, wherein the term "biomaterial" relates to all materials intended for contact with biological tissue or body fluids, e.g. in the course of therapeutic or diagnostic measures.

Subsequent to the preparation of the workpieces 90 in step S0, optionally comprising cleaning the workpieces and arranging same in the recipient 10 as well as subsequently evacuating the recipient, the workpiece surfaces are initially prepared in step S1 for a subsequent coating.

To this end, the recipient 10 loaded with the one or more workpieces is initially evacuated by means of pumps (not shown in the drawings), preferably to a pressure of maximally $10^{-4}$ mbar (10 mPa). After reaching the desired vacuum pressure, the interior 15 is purged with an inert gas, preferably Argon, while continually pumping, wherein the inert gas supply is adjusted to the pumping speed so that in the interior 15 of the recipient 10 a constant pressure is maintained. The inert gas 31 is supplied to the recipient from an inert gas reservoir 21. In embodiments the Argon gas pressure is about 25 mTorr (ca. 3.3 Pa). After reaching a stable inert gas pressure in the interior of the recipient 15, the plasma generator, for example a high-frequency generator, is switched on, whereby an inert gas plasma is generated which surrounds the workpieces 90. The plasma cleans the work piece surfaces by removing substances adsorbed thereon and furthermore results in an activation of the workpiece surfaces by forming ions and free radicals beneficial for the subsequent polymerisation process.

The cleaning and activating effect of this first step S1 may be influenced via the frequency of the generator, the power coupled into the plasma, the exposure time to the plasma, and the type of the inert gas used for the plasma, as is generally known. The settings suitable for each individual application may be determined by the skilled person. In the presently described process, Argon is preferred as the inert gas, because it allows an activation of the workpiece surfaces without generating new, undesired compounds. Naturally, other inert gases may be employed instead, such as nitrogen, if leading to comparable results. In an exemplary embodiment, the exposition time to the Argon plasma is about 1 minute or less. After this time, the plasma generator is switched off and the process continued with the first coating step S2.

Deviating from the above, the plasma employed for the pre-treatment of the workpieces may be generated on the basis of a mixture of the inert gas and a reactive component to be used in a subsequent pre-coating step, instead of pure Argon. The partial pressure of the reactive component in the gas mixture should be less than one tenth than the partial pressure of the inert gas.

On transitioning from step S1 to step S2 of the process, the inert gas supply into the interior of the recipient is preferably maintained or optionally is adjusted so that it assumes a value suitable for carrying out step S2. For generating the gas mixture, a coating material gas made up of biocompatible, polymerizable carboxy group-containing monomers in the vapour phase is admixed to the inert gas in the recipient 10. The carboxy group-containing monomers are preferably acrylic acid or an acrylic acid precursor, such as e.g. (meth)acrylic acid anhydride. The partial pressure $P_{eSG}$ of the first coating material gas in some embodiments is at least one fourth of, and maximally twice the partial pressure $p_{IG}$ of the inert gas. More preferably, the partial pressure ratio $p_{eSG}:p_{IG}$ is selected from the range 1:1 to 1:0.5. For example, the partial pressure of Argon in embodiments of the process is 30 mTorr (ca. 400 mPa) at a total pressure of the gas mixture of 45 mTorr (ca. 600 mPa), resulting in a value of the ratio of the Argon partial pressure $p_{Ar}$ to the first coating material partial pressure (reactive component partial pressure) $P_{eSG}$ of 2:1.

As the reactive component for generating the first coating material gas, preferably (meth)acrylic acid anhydride is used, which is vaporized in one of the reservoirs 22 or 23 in FIG. 1 and is guided to the interior 15 of the recipient 10 via ducts 72 or 73. The partial pressure of the coating material gas is adjusted via its inflow, in turn controlled via valves 42 or 43. Naturally, instead of (meth)acrylic acid anhydride, (meth) acrylic acid may be used. (Meth)acrylic acid or (meth)acrylic acid anhydride are provided in the reservoirs 22 or 23 in liquid form, for example in an amount of 150 ml. In order to prevent or inhibit polymerization of the acrylic acid or its precursor material, respectively, same may be doted with Cu(I)-chloride. Furthermore, the reactive component containers 22 and 23, respectively, after filling are de-aerated until bubbles no longer appear in the reactive component liquid. The vapour pressure of the reactive components at common ambient temperatures of 22 to 25° C. is usually sufficient for forming the first coating material gas.

After adjusting the desired gas mixture and gas mixture pressure the actual pre-coating process is initiated through starting the plasma generator, whereby acrylic acid monomers excited in the plasma attach to the activated workpiece surface and, in the further course, form a poly(acrylic acid) layer. This plasma enhanced pre-coating phase is maintained until a desired coating thickness is reached. The building-up of the coating is continually monitored by means of the coating deposition measuring device 14. In principle, coatings with thicknesses of up to 30,000 nm, corresponding to 30 µm, may be deposited, wherein a respective coating process is terminated once the coating deposition measuring device 14 indicates the achievement of the desired coating thickness within a given tolerance of e.g. 50 to 400 Å. The thickness of the hydrophilic coating to be deposited in the pre-coating process depends on the particular application and in the case of scaffold substances for Tissue Engineering usually is in the range of 30 to 50 nm. For hydrophilizing contact lenses pre-coatings with for example thicknesses in the range of about 5 to 40 nm have proven useful. According to the application and therefore also the required coating thickness, the pre-coating phase may take between 10 and 80 or even 120 minutes. The gas supplies are preferably not varied during the plasma coating. In a first variant of the process, the pre-coating process is terminated by switching off the plasma generator.

Subsequent to the first variant of the pre-coating step S2 described above, a first variant of the follow-up-coating step S3 follows in which, after switching off the plasma generator, initially the inert gas supply is interrupted and the pre-coated workpiece surface is exposed to, if possible, the full vapour pressure of a reactive component formed by water-free acrylic acid. The vapour pressure of the reactive component should not be below 5 Torr (ca. 667 Pa). Slightly cooling or warming the reactive component in the reservoir 22 or 23 may be suitable to adjust the pressure. The introduction of the reactive component into the recipient 10 at full vapour pressure provides the reactive gas in large amounts, which reacts with reactive centers present on the pre-coated surface and provides a relatively thick poly(acrylic acid) layer (PAA-layer), which may be crystalline.

In FIG. 3 a measurement diagram is shown, from which it may be derived that a PAA-layer produced as described above has a thickness of about 10 µm. For this measurement, the hydrophilic PAA-layer was stained with Rhodamin 6G as a fluorescence dye and the fluorescence was measured in dependence of depth by means of confocal microscopy. as may be gathered from the right portion of the fluorescence tracks, the hydrophilic layer extends significantly into the depth of the workpiece. The contact lens measured in FIG. 3 at the site of the measurement has a thickness of 117.5 µm. The resolution of the measurement is 0.6 µm. From the obtained data, it may be derived that a coating thickness on the surface of ca. 10±0.6 µm (region between the vertical lines) and a penetration depth per side of ca. 15 to 20±0.6 µm was present. In the described variant, the process is therefore particularly suitable for the application to silicone contact lenses, for which hydrophilicity of the surface, durability of the coating as well as the optical properties thereof are equally important.

In a second variant of the process, the plasma generator is not switched off at the end of the pre-coating step S2 and is therefore still in operation at the time of transitioning to the follow-up coating step S3. In this variant, the Argon supply is almost or entirely stopped and the supply of the reactive gas, i.e. the acrylic acid, is reduced so much that, with the high-frequency generation maintained and continuously evacuating the recipient 10, a pressure equilibrium in the range of less than 0.3 mTorr (ca. 40 mPa) is achieved. In an exemplary embodiment, the pressure is adjusted to a value of less than 0.1 mTorr (ca. 13 mPa). This follow-up-coating phase is maintained for 5 to 15 minutes and with porous resorbable scaffold substances for Tissue Engineering results in workpiece surfaces having particularly low contact angles for water and excellent cell adhesion rates of e.g. above 90% or above 95%. The described second variant of the process is therefore particularly suitable for the manufacture of coated scaffold substances, which are to be employed for the infiltration of cells in the course of Tissue Engineering.

After terminating the process in step S4 the coated workpieces 90 may be removed from the recipient a may optionally subjected to a quality check.

the process described above allows for a durable hydrophilization of polymeric biomaterial surfaces, which have an excellent wetting with water and, thereby, a high biocompatibility.

The invention claimed is:

1. A process of hydrophilizing surfaces of a porous biocompatible polymeric matrix, the process comprising steps of:
   (a) pre-treating the matrix surface for cleaning and activating the matrix surfaces, and of
   (b) pre-coating the pre-treated matrix surfaces with poly(acrylic acid), and further a step of
   (c) follow-up-coating the pre-coated matrix surfaces with poly(acrylic acid), wherein,
       the pre-treating in step (a) occurs in a high-frequency gas plasma formed on the basis of an inert gas and acrylic acid monomers, the partial pressure of the latter being maximally twice that of the inert gas; and
       the pre-coating with poly(acrylic acid) according to step (c) occurs in the recipient using a gas composition different from the composition of step (b), namely consisting of acrylic acid monomers.

2. The process of claim 1, wherein the gas used in step (a) for generating the high-frequency plasma contains acrylic acid monomers in an amount corresponding to less than one tenth of the partial pressure of the inert gas.

3. The process of claim 1, wherein in the gas mixture used in step (b), the partial pressure of the acrylic acid monomers is at least one fourth the partial pressure of the inert gas.

4. The process of claim 1, wherein the partial pressure of the inert gas in the gas composition used in step (c) is less than one tenth of the partial pressure of the gas formed of acrylic acid monomers.

5. The process of claim 1, wherein Argon forms the inert gas.

6. The process of claim 1, wherein the coating applied in step (b) is monitored by means of a coating thickness monitoring device and is terminated when a coating thickness value selected from the range of 50 to 400 Å is reached.

7. The process of claim 1, wherein the pressure of the inert gas for the high-frequency plasma in step (a) is 15 to 60 mTorr (ca. 2 to 8 Pa) and the pressure of the acrylic acid monomers for the high-frequency plasma in step (b) is 30 to 90 mTorr (ca. 4 to 12 Pa).

8. The process of claim 1, further comprising a step (cb), immediately subsequent to step (b), of throttling the inert gas supply and supplying the acrylic acid monomers, and the pressure of the gas composition in step (c) is less than 0.3 mTorr (ca. 40 mPa).

9. The process of claim 1, further comprising a step (bc), immediately subsequent to step (b) or, if executed, to step (cb), of switching-off the high-frequency plasma, and interrupting the inert gas supply, and supplying the acrylic acid monomers, wherein the pressure of the gas composition in step (c) is between 1.5 and 6 Torr (ca. 0.13 to 0.8 kPa).

10. The process of claim 1, further comprising a step (d) subsequent to step (c) of removing water soluble components from the hydrophilic layer by means of rinsing the coated matrix in a hydrophilic solvent.

11. The process of claim 10, wherein the hydrophilic solvent is isotonic saline solution or demineralized water.

12. The process of claim 1, wherein the matrix is formed of poly($\alpha$-hydroxycarboxylic acids) at least at its surface.

13. The process of claim 12, wherein the matrix is formed of at least one selected from of polylactide (PLA) and polylactide-co-glycolide (PLGA) at least at its surface.

14. The process of claim 13, comprising shaping the matrix as a scaffold for infiltration with cells for tissue engineering before the coating.

15. The process of claim 1, further comprising a step (cb), immediately subsequent to step (b), of stopping the inert gas supply and continuously evacuating the recipient while supplying the second gas to achieve a pressure equilibrium in the range of less than 0.3 mTorr (40 mPa).

16. The process of claim 1, wherein
    a contact angle of water at the matrix surface coated with poly(acrylic acid), PAA, has a value in the range of 2 degrees to below 10 degrees.

17. The process of claim 16, wherein the biocompatible polymeric matrix comprises one or more selected from poly($\alpha$-hydroxycarboxylic acids).

18. The process of claim 17, wherein the poly($\alpha$-hydroxycarboxylic acids) include at least one of polyactide PLA and polyactide-co-glycolide (PLGA).

19. The process of claim 16, wherein the FAA-layer has an average thickness of 5 to 40 nm.

* * * * *